United States Patent [19]

Richard et al.

[11] Patent Number: 5,252,323
[45] Date of Patent: Oct. 12, 1993

[54] S-TRIAZINE COMPOUNDS SUBSTITUTED BY BENZYLIDENECAMPHOR SUBSTITUENTS AND COSMETIC COMPOSITIONS CONTAINING THE S-TRIAZINE COMPOUNDS

[75] Inventors: Herve Richard; Madeleine Leduc, both of Paris; Alex Junino, Livry-Gargan, all of France

[73] Assignee: L'Oreal, Paris, France

[21] Appl. No.: 862,356

[22] Filed: Apr. 2, 1992

[30] Foreign Application Priority Data

Apr. 4, 1991 [FR] France ................. 91 04123

[51] Int. Cl.$^5$ .................. A61K 7/42; A61K 7/44; A61K 7/48; C07D 251/54
[52] U.S. Cl. ............................. 424/59; 424/60; 514/844; 514/845; 514/846; 514/847; 514/848; 544/197
[58] Field of Search ................. 544/197; 424/59, 60; 514/844, 845, 846, 847, 848

[56] References Cited

U.S. PATENT DOCUMENTS

| | | | |
|---|---|---|---|
| 3,577,417 | 5/1971 | Cantrall et al. | 544/197 |
| 3,590,042 | 6/1971 | Cyba | 544/197 |
| 4,061,730 | 12/1977 | Kalopissis et al. | 424/59 |
| 4,250,108 | 2/1981 | Bouillon et al. I | 424/59 X |
| 4,406,880 | 9/1983 | Bouillon et al. II | 424/59 X |
| 4,421,739 | 12/1983 | Bouillon et al. III | 424/59 X |
| 4,617,390 | 10/1986 | Hoppe et al. | 544/197 |
| 4,731,200 | 5/1988 | Lang et al. I | 424/59 X |

FOREIGN PATENT DOCUMENTS

| | | | |
|---|---|---|---|
| 1205970 | 12/1965 | Fed. Rep. of Germany | 544/197 |
| 1200862 | 8/1970 | United Kingdom | 424/59 |
| 2185019 | 7/1987 | United Kingdom | 544/197 |

OTHER PUBLICATIONS

"UV-Filter fur Haut-und Produktschutz in kosmetischen Formulierungen", Siefen et al., vol. 115, #18, Nov. 21 1989, pp. 661-662, Sperling.

2215 Riechstoffe-Aromen-Kosmetica, R.A.K. vol. 32 (Jun. 1982) No. 6, p. 152, Beck et al.

*Primary Examiner*—Floyd D. Higel
*Attorney, Agent, or Firm*—Jacobson, Price, Holman & Stern

[57] ABSTRACT

Compound of formula:

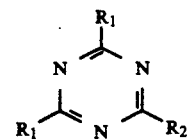

(I)

in which $R_1$ is of the formula:

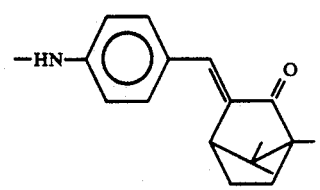

(II)

and $R_2$ is a $C_8$-$C_{20}$ alkoxy or mono- or dialkylamino or is of the formula:

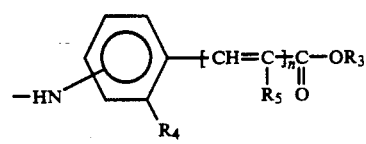

(III)

where n=0 or 1; $R_4$ denotes H, OH or $C_1$-$C_6$ alkoxy; $R_5$ denoted H or $COOR_3$ and $R_3$ is a $C_4$-$C_{20}$ alkyl.

Application of these compounds for the protection of the skin and hair against ultraviolet radiation.

12 Claims, No Drawings

S-TRIAZINE COMPOUNDS SUBSTITUTED BY BENZYLIDENECAMPHOR SUBSTITUENTS AND COSMETIC COMPOSITIONS CONTAINING THE S-TRIAZINE COMPOUNDS

The present invention relates to novel s-triazine derivatives carrying benzylidenecamphor substituents, a method of preparing them and their use as sunscreen agents, in particular in the cosmetic field.

It is known that light radiation of wavelengths between 280 nm and 400 nm permit tanning of the human epidermis and that rays of wavelengths between 280 and 320 nm, known under the name UV-B, cause erythemas and skin burns which can hamper the development of tanning; this UV-B radiation must therefore be screened out.

It is also known that UV-A rays of wavelengths between 320 and 400 nm, which bring about tanning of the skin, are capable of causing damage to it especially in the case of sensitive skin or skin continually exposed to solar radiation. UV-A rays cause in particular loss of elasticity of the skin and the appearance of wrinkles which lead to premature ageing. They promote the onset of erythemal reaction or amplify this reaction in some individuals and may even be responsible for phototoxic or photoallergic reactions.

It is therefore useful to have available compounds which are capable of absorbing both UV-A rays and UV-B rays which are harmful to the skin.

It is also desirable to provide the hair with good protection against photochemical damage in order to avoid, in particular, alteration of shade or bleaching.

It is known moreover that the constituents used in cosmetic preparations do not always possess adequate stability to light and deteriorate under the effect of light radiation.

Consequently, it is desirable to incorporate into these preparations compounds which are capable of screening out UV rays and which should possess in addition good stability and adequate solubility in the media normally used in cosmetics and, in particular, in oils and fats.

s-Triazine derivatives carrying p-aminobenzoate substituents are known from U.S. Pat. No. 4,617,390, which absorb only UV-B radiation and whose solubility in fatty substances is limited; it is therefore necessary, if it is desired to absorb the UV radiation as a whole, to combine UV-A screening agents with these s-triazine derivatives grafted through p-aminobenzoate residues.

Moreover, p-aminobenzylidenecamphor, which is a known compound, may be used as a UV-A screening agent, but this compound has a very low solubility in the fatty substances normally used in cosmetics.

The applicant has discovered that s-triazine derivatives grafted through p-aminobenzylidenecamphor residues absorb, surprisingly, UV-A radiation or UV radiation as a whole (UV-B and UV-A) and at the same time possess good solubility in fatty substances. These s-triazine derivatives also possess a very high molar absorption coefficient which makes it possible to use them in a low concentration, for example in cosmetic skin protection or antisun compositions.

Furthermore, combined with dibenzoylmethane-type UV-A screening agents, especially 4-tert-butyl-4'-methoxy-dibenzoylmethane (Parsol 1789), these novel s-triazine derivatives permit these UV-A screening agents to be photostabilised.

In addition to their screening properties and their fat solubility, these novel s-triazine derivatives possess good chemical and photochemical stability and have the advantage of being neither toxic nor irritant and of being perfectly innocuous towards the skin.

The subject of the present invention is therefore novel compounds of the following formula (I):
in which $R_1$ is of the formula:

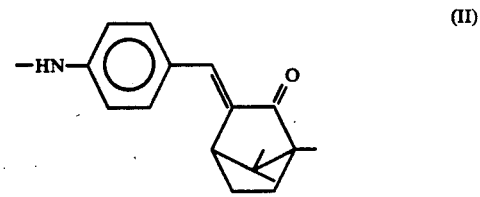

and $R_2$ is a linear or branched alkoxy or mono- or dialkyl-amino group containing 8 to 20 carbon atoms or is of the formula (III):

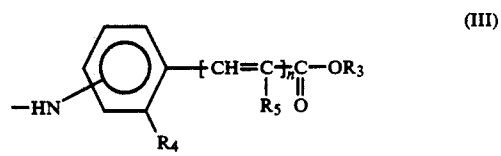

in which n is equal to 0 or 1;

when n is equal to 0, $R_3$ is a linear or branched alkyl radical containing 8 to 20 carbon atoms; $R_4$ represents a hydrogen atom, the amino residue being in position 4 with respect to the carboxyl group, or $R_4$ represents a hydroxyl radical or a $C_1$-$C_6$ alkoxy radical, the amino residue being in position 4 or 5 with respect to the carboxyl group;

when n is equal to 1, $R_3$ is a linear or branched alkyl radical containing 4 to 20 carbon atoms; $R_4$ represents a hydrogen atom, the amino residue being in position 4 with respect to the unsaturated group, $R_5$ is a hydrogen atom or a group $COOR_3$ in which $R_3$ has the meaning given above for $n=1$, provided that when $R_5$ is a hydrogen atom, $R_3$ should contain 8 to 20 carbon atoms.

Among the linear or branched alkyl radicals, there may be mentioned for example: n-butyl, isobutyl, tert-butyl, n-amyl, isoamyl, neopentyl, n-hexyl, n-heptyl, n-octyl, 2-ethylhexyl, n-dodecyl and n-octadecyl.

Among the linear or branched alkoxy radicals, there may be mentioned for example: methoxy, ethoxy, n-propoxy, isopropoxy, n-butoxy, isobutoxy, tert-butoxy, n-amyloxy, isoamyloxy, neopentyloxy, n-hexyloxy, n-heptyloxy, n-octyloxy, 2-ethylhexyloxy, n-dodecyloxy and n-octadecyloxy.

The compounds (I) absorb UV-A radiation when $R_2$ is an alkoxy or a mono- or dialkylamino group or is of the formula (III) in which n is equal to 1, or n is equal to 0 and $R_4$ represents a hydroxyl radical, the amino residue being in position 5 with respect to the carboxyl group, or they absorb broad-band UV radiation (UV-A and UV-B) in the other cases.

These novel s-triazine derivatives may be used as sunscreen agents for human skin and for the hair and as light-protecting agents in the plastics industry.

The subject of the present invention is also the method of preparing the compounds of formula (I).

The compounds of formula (I) may be obtained according to the reaction scheme below:

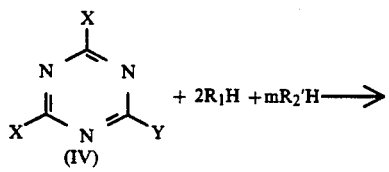

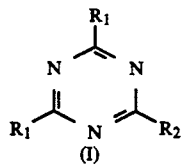

where $R_1$ is of the formula (II) which is given above, $R'_2$ is of the formula (III) and $R_2$ has the meaning given above; X represents a halogen, in particular chlorine or bromine, Y represents X, a linear or branched alkoxy or mono- or dialkylamino group containing 8 to 20 carbon atoms; m is an integer equal to 1 if Y is equal to X, the reaction being carried out in 2 stages; if Y is different from X, m is equal to 0.

The compounds of general formula (IV) in which Y is different from X may be obtained according to the reaction scheme below, which is described in the publications: J. T. THURSTON et al., J. Am. Chem. Soc., 73, 2981 (1951) and J. R. DUDLEY et al., J. Am. Chem. Soc. 73, 2986 (1951):

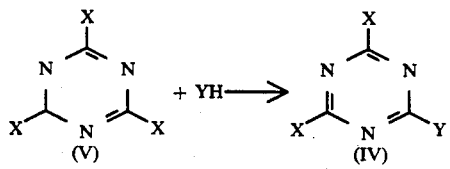

X and Y having the same meanings as above.

The reactions may be carried out optionally in the presence of a solvent (for example: toluene, xylene or acetone/water), at a temperature between 0° and 250° C., more particularly between 0° and 150° C.

The compounds $R'_2H$ where $R'_2$ is of the formula (III) may be prepared according to known methods described in Patents FR-2,151,503, FR-A 2,385,685 and GB 1,064,116.

The compound $R_1H$ where $R_1$ is of the formula (II) may be prepared as indicated by HALLER, BOUDIN, Annales de Chimie, 9th series, volume XVII (1922).

Among the compounds of formula (I) above, the following compounds may be mentioned more particularly:

1) .2,4-bis(4'-aminobenzylidenecamphor)-6-(2-ethylhexylamino)-s-triazine
2) .2,4-bis(4'-aminobenzylidenecamphor)-6-(diisobutyl 4'-aminobenzalmalonate)-s-triazine
3) .2,4-bis(4'-aminobenzylidencamphor)-6-(2-ethylhexyl 5'-aminosalicylate)-s-triazine.

By virtue of their fat solubility, the compounds of formula (I) above become uniformly distributed in conventional cosmetic carriers containing at least one cosmetically acceptable fatty phase or organic solvent, and may be applied to the skin or the hair to form an effective protective film.

The subject of the present invention is therefore also a cosmetic composition containing, in a cosmetically acceptable carrier containing at least one fatty phase or one organic solvent, an effective amount of at least one compound of formula (I) above.

The cosmetic composition of the invention may also be used as human epidermis- or hair-protecting composition or as antisun composition.

The subject of the present invention is also a method of protecting the skin and natural or sensitised against hair solar radiation, which consists in applying to the skin or the hair an effective amount of a cosmetic composition containing at least one compound of formula (I).

"Sensitised hair" is understood to mean hair which has undergone permanent wave, dyeing or bleaching treatment.

The subject of the invention is also a coloured or colourless cosmetic composition, stabilised with respect to light, containing an effective amount of at least one compound of formula (I) above.

When it is used as a composition intended for protecting the human epidermis against ultraviolet rays, the cosmetic composition according to the invention may be provided in the most diverse forms normally used for this type of composition. It may in particular be provided in the form of oily or oil-alcohol lotions, emulsions such as a cream or a milk, vesicular dispersions of ionic or nonionic amphiphilic lipids, oil-alcohol or alcoholic gels, solid sticks or they may be packaged as an aerosol. The creams constitute what is generally called "protective day creams" for daily use.

It may contain the cosmetic adjuvants normally used in this type of composition, such as thickeners, demulcents, humectants, surface-active agents, preservatives, antifoams, perfumes, oils, waxes, lanolin, propellants, colorants and/or pigments whose role is to colour the composition itself or the skin, or any other ingredient normally used in cosmetics. It may in addition contain other UV-A and/or UV-B screening agents.

The compound of formula (I) is present in proportions by weight between 0.1 and 2% relative to the total weight of the cosmetic human epidermis-protecting composition.

An oil, a wax and generally any fatty substance, a lower monoalcohol or polyol or mixtures thereof, may be used as solubilising solvent. The monoalcohols or polyols more particularly preferred are ethanol, isopropanol, propylene glycol, hexylene glycol, glycerin and sorbitol.

One embodiment of the invention is an emulsion in the form of a protective cream or milk containing, in addition to the compound of formula (I), fatty alcohols, fatty acid esters and in particular fatty acid triglycerides, fatty acids, lanolin, natural or synthetic oils or waxes and emulsifiers, in the presence of water.

The vesicular dispersion of ionic or nonionic amphiphilic lipids may be prepared according to known methods.

The lipids may for example be swollen in an aqueous solution to form spherules dispersed in the aqueous medium as described in the article BANGHAN, STANDISH & WATKINS, J. Mol. Biol., 13,238 (1965) or in Patents FR-2,315,991 and 2,416,008 by the applicant.

Another embodiment consists of oily lotions based on natural or synthetic oils and waxes, lanolin and fatty acid esters, in particular fatty acid triglycerides, or of oil-alcohol lotions based on a lower alcohol such as ethanol or a glycol such as propylene glycol and/or a polyol such as glycerin and oils, waxes and fatty acid esters such as fatty acid triglycerides.

The cosmetic composition of the invention may also be an alcoholic gel containing one or more lower alcohols or polyols such as ethanol, propylene glycol or glycerin and a thickener such as silica. The oil-alcohol gels in addition contain a natural or synthetic oil or wax.

The solid sticks consist of natural or synthetic waxes and oils, fatty alcohols, fatty acid esters, lanolin and other fatty substances.

Conventional propellants are used in the case of a composition packaged as an aerosol.

The present invention also relates to cosmetic antisun compositions containing at least one compound of formula (I) and which may contain other UV-B and/or UV-A screening agents.

In this case, the total amount of screening agents present in the antisun composition, that is to say the compound of formula (I) and, optionally, the other screening agents, is between 0.3 and 15% by weight relative to the total weight of the antisun composition.

These antisun compositions are provided in the forms indicated above for the human epidermis-protecting compositions.

As sunscreen agents screening out UV-B rays, there may be mentioned water-soluble screening agents such as the benzylidenecamphor derivatives described in French Patents 2,199,971; 2,236,515; 2,282,426 and 2,383,904, by the applicant, and more particularly 4-(2-oxo-3-bornylidenemethyl)phenyltrimethylammonium methyl sulphate, and the salts of 4-(2-oxo-3-bornylidenem-methyl)benzenesulphonic acid, 2-methyl-5-(2-oxo-3-bornylidenemethyl)benzenesulphonic acid, 3-benzylidene-2-oxo-10-bornanesulphonic acid and 2-phenylbenzimidazole-5-sulphonic acid.

The compounds according to the invention may also be combined with UV-B screening agents consisting of fat-soluble compounds or of oils having screening properties, such as in particular coffee oil. As fat-soluble UV-B sunscreen agents, there may be mentioned salicylic acid derivatives such as 2-ethylhexyl salicylate or homomethyl salicylate, cinnamic acid derivatives such as 2-ethyl-hexyl p-methoxycinnamate or 2-ethoxyethyl p-methoxycinnamate, p-aminobenzoic acid derivatives such as amyl p-aminobenzoate or 2-ethylhexyl p-dimethylaminobenzoate, benzophenone derivatives such as 2-hydroxy-4-methoxy-benzophenone or 2,2'-dihydroxy-4-methoxybenzophenone, camphor derivatives such as 3-(4'-methylbenzylidene)-camphor or 3-benzylidenecamphor.

The compounds according to the invention may also be combined with UV-A screening agents among which there may be mentioned dibenzoylmethane derivatives, for example 2-methyldibenzoylmethane, 4-methyldibenzoyl-methane, 4-isopropyldibenzoylmethane, 4-tert-butyldiben-zoylmethane, 2,4-dimethyldibenzoylmethane, 2,5-dimethyl-dibenzoylmethane, 4,4'-diisopropyldibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane and 2,6-dimethyl-4-tert-butyl-4'-methoxydibenzoylmethane, as well as 1,4-benzene[di(3-methylidenecamphor)]derivatives sulphonated on the methyl radical in position 10 of the camphor such as described in French Patents 2,528,420 and 2,639,347.

It is understood that the abovementioned list of sunscreen agents used in combination with the compounds (I) according to the invention is not limiting.

When the cosmetic composition according to the invention is intended for protecting natural or sensitised hair from UV rays, this composition may be provided in the form of a shampoo, lotion, rinse-off gel or emulsion to be applied before or after shampooing, before or after dyeing or bleaching, or before or after permanent waving, hair styling or treating lotion or gel, blow drying or hair setting lotion or gel, hair lacquer, composition for permanent waving, dyeing or bleaching of hair. This composition may contain, in addition to the compound of the invention, various adjuvants used in this type of composition, such as surface-active agents, thickeners, polymers, demulcents, preservatives, foam stabilisers, electrolytes, organic solvents, silicone derivatives, oils, waxes, anti-fat agents, colorants and/or pigments whose role is to colour the composition itself or the hair, or any other ingredient normally used in hair care.

It contains 0.1 to 2% by weight of the compound of formula (I).

The present invention also relates to cosmetic compositions containing at least one compound of formula (I) as protective agent against ultraviolet rays, consisting of hair compositions such as hair lacquers, hair setting lotions, optionally, for treating or disentangling, dyeing shampoos, hair dyeing compositions; of make-up products such as nail varnishes, epidermal treatment creams and oils, foundations, lipsticks, skin care compositions such as bath oils or creams, as well as any other cosmetic composition which may present problems of stability to light during storage because of its constituents.

Such compositions contain 0.1 to 2% by weight of the compound of formula (I).

The compounds (I) according to the invention may also be incorporated into various organic materials, and in particular plastics, for the purpose of protecting them against ultraviolet radiation.

The invention will be better illustrated, without however being limited, by the following exemplary embodiments.

EXAMPLE 1

2,4-bis(4'-Aminobenzylidenecamphor)-6-(2-ethylhexylamino)-s-triazine

Preparation of the starting 2-(2-ethylhexylamino)-4,6-dichloro-s-triazine (IV)

A solution of cyanuric chloride (0.2 mol, 36.8 g) in acetone (300 ml) is introduced dropwise into crushed ice (100 g) in a round-bottom flask, with vigorous stirring, followed by a solution of 2-ethylhexylamine in acetone (100 ml), while maintaining the temperature between 0° and 5° C., and finally a solution of sodium carbonate (11.2 g, 0.1 mol) in 300 ml of water. The mixture is left stirring for one hour at 0°–5° C. The oil is extracted with dichloromethane and the organic phase is washed with water and dried over sodium sulphate. After evaporation of the solvent, 2-(2-ethylhexylamino)-4,6-dichloro-s-triazine (52 g, yield=95%) having the following characteristics is obtained:

white powder
m.p.=37° C.
analysis: $C_{11}H_{18}Cl_2N_4$

|  | C % | H % | Cl % | N % |
|---|---|---|---|---|
| Calculated: | 47.66 | 6.55 | 25.58 | 20.21 |
| Found: | 47.89 | 6.60 | 25.79 | 20.16 |

Preparation of the compound (I)

The above derivative (16.6 g, 0.06 mol) is refluxed in xylene (300 ml), under nitrogen, for 6 hours, with 4-aminobenzylidenecamphor (33.7 g, 0.132 mol). After cooling, the solid is filtered and washed with xylene and with diisopropyl ether. After two recrystallisations from absolute ethanol, the compound (20.5 g) having the following characteristics is obtained:
  pale yellow powder
  UV: (95% ethanol) $\lambda_{max}=354$ nm ($\epsilon_{max}=67,100$)
  analysis: $C_{45}H_{58}N_6O_2$

|  | C % | H % | N % | O % |
|---|---|---|---|---|
| Calculated: | 75.59 | 8.18 | 11.75 | 4.48 |
| Found: | 75.68 | 8.23 | 11.88 | 4.53 |

EXAMPLE 2

2,4-bis(4'-Aminobenzylidenecamphor)-6-(diisobutyl 4'-aminobenzalmalonate)-s-triazine 1st stage Preparation of 2,4-bis(4'-aminobenzylidenecamphor)-6 chloro-s-triazine 4-Aminobenzylidenecamphor (12.76 g, 0.05 mol) in solution in 75 ml of acetone is added dropwise at 35°–40° C. to a solution of cyanuric chloride (4.61 g, 0.025 mol) in 50 ml of acetone followed, dropwise, by 50 ml of N sodium hydroxide over 2 hours. Stirring is maintained for 1.5 hours. After draining the precipitate, washing with water and drying, 2,4-bis(4'-aminobenzylidenecamphor)-6-chloro-s-triazine (12.6 g, yield=81%) having the following characteristics is obtained:
  pale yellow powder
  m.p.=255° C.
  UV: (95% ethanol) $\lambda_{max}=346$ nm ($\epsilon_{max}=61,900$)
  analysis: $C_{37}H_{40}ClN_5O_2$

|  | C % | H % | Cl % | N % | O % |
|---|---|---|---|---|---|
| Calculated: | 71.42 | 6.48 | 5.70 | 11.26 | 5.14 |
| Found: | 71.43 | 6.51 | 5.66 | 11.15 | 5.35 |

2nd stage

Preparation of the compound (I)

The above derivative (3.11 g, 0.005 mol) and diisobutyl 4-aminobenzalmalonate (1.6 g, 0.005 mol) are refluxed for 10 hours, under nitrogen, in 24 ml of xylene. The mixture is cooled and neutralised with a saturated solution of sodium bicarbonate. The organic phase is washed with water, dried over sodium sulphate and concentrated. The oil obtained is chromatographed on a silica column (eluent CH$_2$Cl$_2$). The compound (3.5 g, yield=78%) having the following characteristics is obtained:
  pale yellow powder
  m.p.=186° C.
  UV: (95% ethanol) $\lambda_{max}=358$ nm ($\epsilon_{max}=106,350$)
  analysis: $C_{55}H_{64}N_6O_6$

|  | C % | H % | N % | O % |
|---|---|---|---|---|
| Calculated: | 72.98 | 7.13 | 9.28 | 10.61 |
| Found: | 72.68 | 7.18 | 9.11 | 11.01 |

EXAMPLE 3

2,4-bis(4'-Aminobenzylidenecamphor)-6-(2-ethylhexyl 5'-aminosalicylate)-s-triazine 2,4-bis(4'-Aminobenzylidenecamphor)-6-chloro-s-triazine, prepared in the 1st stage of Example 2 (3.11 g, 0.005 mol) and 2-ethylhexyl 5'-aminosalicylate (1.32 g, 0.005 mol) are refluxed for 6 hours, under nitrogen, in 24 ml of xylene. After cooling, the mixture is neutralised with a saturated solution of sodium bicarbonate. The organic phase is washed twice with water, dried over sodium sulphate and concentrated. The oil obtained is purified on a silica column (eluent: CH$_2$Cl$_2$). The product (3.8 g, yield=89%) having the following characteristics is obtained:
  m.p.=melting towards 150° C.
  UV: (95% ethanol) $\lambda_{max}=355$ nm ($\epsilon_{max}=76,340$)
  analysis: $C_{52}H_{62}N_6O_5$

|  | C % | H % | N % | O % |
|---|---|---|---|---|
| Calculated: | 73.38 | 7.34 | 9.87 | 9.40 |
| Found: | 73.34 | 7.32 | 9.76 | 9.43 |

EXAMPLE A

Antisun Oil

The following ingredients are mixed while optionally heating to 40°–45° C. to homogenise:

| Liquid paraffin | 2.5 g |
|---|---|
| Compound of Example 2 | 2.0 g |
| 2-Ethylhexyl p-dimethylaminobenzoate | 4.0 g |
| Ditert-butylhydroxytoluene | 0.05 g |
| Perfume qs |  |
| C$_8$–C$_{12}$ fatty acid triglycerides "MIGLYOL 812" (company DYNAMIT NOBEL) | 40.0 g |
| Alcohol, 96% qs | 100.0 g |

EXAMPLE B

Antisun Oil-In-Water Emulsion

| Compound of Example 2 | 1.5 g |
|---|---|
| 2-Ethylhexyl para-methoxycinnamate | 2.0 g |
| Mixture of cetylstearyl alcohol and oxyethylenated cetylstearyl alcohol containing 33 mol of ethylene oxide ("SINNOWAX AO") sold by HENKEL | 7.0 g |
| Glycerol monostearate | 2.0 g |
| Propylene glycol | 10.0 g |
| Cetyl alcohol | 1.3 g |
| C$_{12}$–C$_{15}$ fatty alcohol benzoate ("FINSOLV TN" sold by WITCO) | 15.0 g |
| Preservative | 0.2 g |
| Perfume qs |  |
| Deionised water qs | 100.0 g |

The emulsion is prepared in the following manner:

2Ethylhexyl p-methoxycinnamate and the derivative of Example 2 are dissolved in the fatty phase which is heated to around 70°-75° C. On the other hand, water containing the water-soluble compounds is heated to 70°-75° C. and the fatty phase is added to the aqueous phase. After stirring vigorously for 10 minutes, the mixture is allowed to cool while stirring gently, and the preservative and the perfume are added at around 40° C.

EXAMPLE C

Hair-Protecting Oil

| | |
|---|---|
| Compound of Example 3 | 1.0 g |
| Oleyl alcohol | 19.5 g |
| Hexylene glycol | 0.5 g |
| Colza oil qs | 100.0 g |

This oil, of opalescent appearance, is applied to dry hair, to which it gives sheen and softness while preserving its colour when it is exposed to natural light.

EXAMPLE D

Protective Hair Cream

| | |
|---|---|
| Compound of Example 1 | 0.5 g |
| Oxyethylenated cetylstearyl alcohol containing 33 mol of ethylene oxide | 4.0 g |
| Cetyl alcohol | 2.0 g |
| Stearyl alcohol | 2.0 g |
| Cationic cellulose ether sold under the name "JR 400" by UNION CARBIDE | 0.5 g |
| Water qs | 100.0 g |

This emulsion is prepared as in Example B.
Applied to wet hair, it facilitates disentangling. The dry hair is soft and protected from the sun.

EXAMPLE E

Protective Day Cream

| | |
|---|---|
| Mixture of cetylstearyl alcohol and oxyethylenated cetylstearyl alcohol containing 33 mol of ethylene oxide sold under the name "SINNOWAX AO" by HENKEL | 7.0 g |
| Mixture of glycerol mono- and distearate, non-self-emulsifying | 2.0 g |
| Cetyl alcohol | 1.5 g |
| Silicone oil | 1.5 g |
| Oxypropylenated myristyl alcohol containing 3 mol of propylene oxide sold under the name "WITCONOL APM" by WITCO | 20.0 g |
| 4-tert-Butyl-4'-methoxydibenzoylmethane sold under the name "PARSOL 1789" by GIVAUDAN | 1.0 g |
| Compound of Example 1 | 1.0 g |
| Glycerin | 20.0 g |
| Perfume, preservatives qs | |
| Water qs | 100.0 g |

The emulsion is prepared in the same manner as in Example B.

EXAMPLE F

Protective Day Cream

| | |
|---|---|
| Mixture of cetylstearyl alcohol and oxyethylenated cetylstearyl alcohol containing 33 mol of ethylene oxide sold under the name "SINNOWAX AO" by HENKEL | 7.0 g |
| Mixture of glycerol mono- and distearate, non-self-emulsifying | 2.0 g |
| Cetyl alcohol | 1.5 g |
| Silicone oil | 1.5 g |
| Oxypropylenated myristyl alcohol containing 3 mol of propylene oxide sold under the name "WITCONOL APM" by WITCO | 20.0 g |
| Compound of Example 1 | 2.0 g |
| Glycerin | 20.0 g |
| Perfume, preservatives qs | |
| Water qs | 100.0 g |

The emulsion is prepared in the same manner as in Example B.

EXAMPLE G

Protective Day Cream

| | |
|---|---|
| Mixture of cetylstearyl alcohol and oxyethylenated cetylstearyl alcohol containing 33 mol of ethylene oxide sold under the name "SINNOWAX AO" by HENKEL | 7.0 g |
| Mixture of glycerol mono- and distearate, non-self-emulsifying | 2.0 g |
| Cetyl alcohol | 1.5 g |
| Silicone oil | 1.5 g |
| Oxypropylenated myristyl alcohol containing 3 mol of propylene oxide sold under the name "WITCONOL APM" by WITCO | 20.0 g |
| Glycerin | 20.0 g |
| 1,4-benzene[di(3-methylidene-10-camphor-sulphonic)] acid | 1.0 g AI |
| Compound of Example 1 | 1.0 g |
| Triethanolamine | 0.6 g |
| Perfume, preservatives qs | |
| Purified water qs | 100.0 g |

This oil-in-water emulsion is prepared in the same manner as in Example B.

We claim:

1. A Compound of formula:
in which $R_1$ is of the formula:

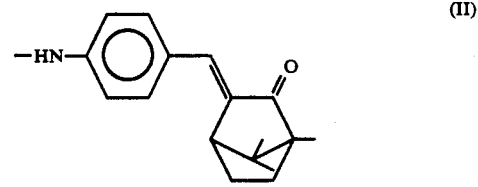
(II)

and $R_2$ is a linear or branched alkoxy or mono- or dialkyl-amino group containing 8 to 20 carbon atoms or is of the formula (III):

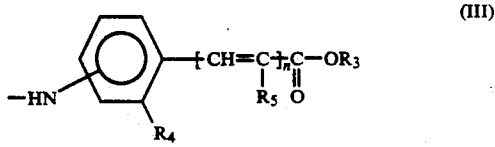
(III)

in which n is equal to 0 or 1;
when n is equal to 0, $R_3$ is a linear or branched alkyl radical containing 8 to 20 carbon atoms; $R_4$ represents a hydrogen atom, the amino substituent being in position 4 with respect to the carboxyl group, or $R_4$ represents a hydroxyl, radical or a $C_1$–$C_6$ alkoxy radical, the amino substituent being in position 4 or 5 with respect to the carboxyl group;

when n is equal to 1, $R_3$ is a linear or branched alkyl radical containing 4 to 20 carbon atoms, $R_5$ is a hydrogen atom or a group $COOR_3$ where $R_3$ is a linear or branched alkyl radical which contains 4 to 20 carbon atoms; $R_4$ represents a hydrogen atom, the amino substituent being in position 4 with respect to the unsaturated group, provided that when $R_5$ is a hydrogen atom, $R_3$ contains 8 to 20 carbon atoms.

2. A Compound according to claim 1, which is selected from the group consisting of:
1) .2,4-bis(4′-aminobenzylidenecamphor)-6-(2-ethylhexylamino)-s-triazine,
2) .2,4-bis(4′-aminobenzylidenecamphor)-6-(diisobutyl 4′-aminobenzalmalonate)-s-triazine, and
3) .2,4-bis(4′-aminobenzylidencamphor)-6-(2-ethylhexyl 5′-aminosalicylate)-s-triazine.

3. A Cosmetic composition which contains an effective amount of at least one compound of formula (I) according to claim 1, in a cosmetically acceptable carrier containing at least one fatty phase or one organic solvent.

4. A Cosmetic composition according to claim 3, which contains at least one of the compounds selected from the group consisting of:
1) .2,4-bis(4′-aminobenzylidenecamphor)-6-(2-ethylhexylamino)-s-triazine,
2) .2,4-bis(4′-aminobenzylidenecamphor)-6-(diisobutyl 4′-aminobenzalmalonate)-s-triazine, and
3) .2,4-bis(4′-aminobenzylidencamphor)-6-(2-ethylhexyl 5′-aminosalicylate)-s-triazine.

5. A Cosmetic composition according to claim 3 in the form of an oily or oil-alcohol lotion, emulsion, oil-alcohol or alcoholic gel, vesicular dispersion, solid stick or aerosol.

6. A Cosmetic composition according to claim 5, which further contains cosmetic adjuvants selected from the group consisting of: thickeners, demulcents, humectants surface-active agents, preservatives, antifoams, perfumes, oils, waxes, lanolin, lower monoalcohols and polyols, propellants, colorants and pigments.

7. A Cosmetic human epidermis-protecting composition according to claim 3 which
contains 0.1 to 2% by weight of a compound of formula (I).

8. A Cosmetic antisun composition according to claim 3 which contains 0.3 to 15% by weight of a compound of formula (I).

9. A Cosmetic antisun composition according to claim 8, which further contains an agent screening out UV-B and/or UV-A rays which is different from the compound of formula (I).

10. A Cosmetic composition according to claim 3 intended to be applied to hair, in the form of a shampoo, lotion, rinse-off gel or emulsion, hair styling or treating lotion or gel, blow drying or hair setting lotion or gel, hair lacquer, permanent wave, bleaching or dyeing composition, and which contains 0.1 to 2% by weight of a compound of formula (I).

11. A Cosmetic composition according to claim 3 in the form of a cosmetic composition stabilised with respect to light, which consists of a hair composition, a make-up product or a skin care or treatment composition, containing 0.1 to 2% by weight of a compound of formula (I).

12. A Method of protecting the skin and natural or sensitised hair against ultraviolet radiation, which consists in applying to the skin or the hair an effective amount of a cosmetic composition containing at least one compound of formula (I) according to claim 1.

* * * * *